United States Patent [19]

Guglielmetti et al.

[11] 4,138,429

[45] Feb. 6, 1979

[54] PROCESS FOR THE MANUFACTURE OF O-PHENYLENEDIACETONITRILE

[75] Inventors: Leonardo Guglielmetti, Basel; Alain C. Rochat, Birsfelden; Ian J. Fletcher, Magden, all of Switzerland

[73] Assignee: Ciba-Geigy Corporation, Ardsley, N.Y.

[21] Appl. No.: 834,083

[22] Filed: Sep. 19, 1977

[30] Foreign Application Priority Data

Sep. 29, 1976 [CH] Switzerland ............... 12298/76

[51] Int. Cl.$^2$ .............. C07C 120/04; C07C 121/66
[52] U.S. Cl. ........................................... 260/465 H
[58] Field of Search ................................. 260/465 H

[56] References Cited

U.S. PATENT DOCUMENTS

| 3,992,432 | 11/1976 | Napier et al. ............... 260/465.1 |
| 4,011,261 | 3/1977 | Guglielmetti et al. ...... 260/465 H X |
| 4,056,509 | 11/1977 | Verbrugge et al. ............ 260/465 G |

OTHER PUBLICATIONS

Moore et al., J. Chem. Soc., 93, pp. 165-187 (1908).
Fieser et al., J. Amer. Chem. Soc., 68, pp. 2577-2580 (1946).
Cope et al., J. Amer. Chem. Soc., 73, pp. 1668-1673 (1951).
Schroth et al., Annalen der Chemie, 639, pp. 214-228 (1961).
Rosowsky et al., J. Heterocyclic Chem., 6, pp. 613-622 (1969).
Kobler, Synthesis, pp. 605-607, (Sep. 1975).

*Primary Examiner*—Dolph H. Torrence
*Attorney, Agent, or Firm*—Edward McC. Roberts; Prabodh I. Almaula

[57] ABSTRACT

A process for the manufacture of o-phenylenediacetonitrile by reacting an aqueous solution of an alkali metal or alkaline earth metal cyanide with an o-xylylene halide optionally in the presence of an emulsifier is provided.

4 Claims, No Drawings

PROCESS FOR THE MANUFACTURE OF O-PHENYLENEDIACETONITRILE

The present invention relates to a process for the manufacture of o-phenylenediacetonitrile.

Various process for the manufacture of o-phenylenediacetonitrile are known from the literature. For example, C. W. Moore and J. F. Thorpe [J. Chem. Soc. 93, 165 (1908)], L. F. Fieser and M. M.Pechet [J. Amer. Chem. Soc. 68, 2577 (1946)] and W. Schroth and W. Treibs [Annalen der Chemie 639, 214 (1961)] describe the manufacture of o-phenylenediacetonitrile from o-xylylene dibromide and tetraethylammonium chloride in methylene chloride. A. Rosowsky, A. S. Dey, J. Battaglia and E. J. Modest [J. Heterocyclic Chem. 6, 613 (1969)] describe the manufacture of substituted o-xylylene dicyanides from o-xylylene dichlorides and sodium cyanide in anhydrous dimethyl sulphoxide.

It has now been found that o-phenylenediacetonitrile can also be obtained from o-xylylene halides and alkali metal or alkaline earth metal cyanides in the absence of organic solvents.

The process of the present invention for the manufacture of o-phenylenediacetonitrile by reaction of o-xylylene halides with alkali metal or alkaline earth metal cyanides comprises reacting an aqueous solution of an alkali metal or alkaline earth metal cyanide with an o-xylylene halide in the presence or absence of an emulsifier. Preferably the reaction is carried out in the presence of an emulsifier. The term "halide" is to be understood as meaning chloride, fluoride, and bromide, preferably chloride and bromide.

In a preferred embodiment of the process of the invention, the fused o-xylylene halide is added to the aqueous solution of alkali metal or alkaline earth metal cyanide which contains the emulsifier.

The aqueous solutions of alkali metal or alkaline earth metal cyanide employed are preferably concentrated solutions. Preferably, 2 to 4 molar equivalents of cyanide are used per mole of o-xylylene halide.

Suitable emulsifiers are non-ionogenic, cationic and anionic compounds.

Suitable non-ionogenic emulsifiers are the ethylene oxide reaction products of higher fatty acids, fatty alcohols, fatty acid amides and fatty amines. The ethoxylation products of the higher amines can be in the form of their salts with lower carboxylic acids, such as acetic, formic or propionic acid, or with mineral acids, such as hydrochloric or sulphuric acid.

As examples of such non-ionogenic emulsifiers there may be mentioned: ethoxylated coconut fatty amine with 5 or 15 moles of ethylene oxide, ethoxylated stearyl- or oleylamine with 5, 10 or 30 moles of ethylene oxide, ethoxylated dodecyl- and hexadecylamine with 6 moles of ethylene oxide, and the acetates or chlorides of these compounds, ethoxylated (N-stearyl)- or (N-hexadecyl)-trimethylenediamine with 10 moles of ethylene oxide, ethoxylated oleic acid monoethanolamide with 4 moles of ethylene oxide, ethoxylated stearic acid amide with 12 moles of ethylene oxide, ethoxylated coconut fatty acid propanolamide with 15 or 25 moles of ethylene oxide, ethoxylated oleic acid monoethylamine with 10 moles of ethylene oxide, ethoxylated cetyl, stearyl and oleyl alcohol with 10 or 25 moles of ethylene oxide and lauric, palmitic, stearic, oleic, behenic and ricinolic acid with 10, 15 or 30 moles of ethylene oxide. As the examples show, the hydrocarbon radicals of the ethoxylated compounds can be both saturated and unsaturated and contain at least 12 carbon atoms in the chain. The chain can also be substituted for example by OH groups. Preferably, those emulsifiers are used which contain 12 to 20 carbon atoms in the hydrocarbon radical and are ethoxylated with 5 to 15 moles of ethylene oxide.

Cationic emulsifiers are in particular quaternary phosphonium and ammonium compounds. Examples of such compounds are: dodecyl tri-n-butylphosphonium bromide, cetyl- or laurylbenzyldimethylammonium chloride, cetyltrimethylammonium bromide, benzyl tri-n-butylammonium bromide, hexadecyl-(dichlorobenzyl)-dimethylammonium chloride, octadecyloxymethyl chloride and hexadecyloxymethylpyridinium chloride and also lauryloxymethyl-N-β-hydroxyethylmorpholinium chloride. The emulsifiers mentioned in German Offenlegungsschrift No. 2,161,602 are also suitable.

It is also possible to use anionic emulsifiers, for example alkylsulphonates and alkylarylsulphonates, dialkylsulphosuccinates and alkyl sulphates. By way of example, octyl sulphonate, dodecyl and octadecyl sulphonate, mineral oil and paraffin sulphonate, di-(2-ethylhexyl)- and di-(tridecyl)-sodium sulphosuccinate, as well as cetyl and oleyl sulphate, may be mentioned. For neutralisation of the sulphonates and sulphates, it is also possible to use amines, such as propylamine, monoethanolamine and triethanolamine, in addition to the conventional aqueous alkaline solutions (sodium hydroxide or potassium hydroxide solution).

The emulsifier is used in catalytic amounts, for example 0.01 to 10, preferably 0.1 to 5, molar percent, referred to the o-xylylene halide. The reaction of the present invention is carried out at temperatures above the melting point of the o-xylylene halide employed, in particular at temperatures between 20° and 110° C. and, when o-xylylene dichloride is used, preferably between 50° and 70° C. Preferably an excess of 2 to 10% of the solution of alkali metal cyanide, preferably sodium or potassium cyanide solution, is used.

The process of the present invention results in o-phenylenediacetonitrile being obtained in higher yield and greater purity than by means of the known processes. Compared with the known processes, the process of the invention is much more economical, since it is no longer necessary to use solvents and, in particular, because the omission of solvents, especially of dimethyl sulphoxide, makes it possible to remove the difficulties of solvent recovery and to eliminate the necessary excess of cyanide.

o-Phenylenediacetonitrile is an important intermediate for the manufacture of fluorescent brighteners, fluorescent dyes, dyes and plastics, after it has been reacted, if desired, in a manner known per se to give the corresponding 1,4-naphthalenedicarboxylic acid derivatives. Naphthalene-1,4-dicarboxylic acid can also be prepared direct by means of the process of the invention, i.e. without isolating the o-phenylenediacetonitrile. Examples of such fluorescent brighteners are given in German Offenlegungsschrift No. 2,237,874 and U.S. Pat. No. 3,709,896, and the use of naphthalene-1,4-dicarboxylic acid for the manufacture of polyamides is described in French Pat. No. 876,655.

The invention is illustrated by the following Examples, in which the parts and percentages are by weight unless otherwise indicated.

EXAMPLE 1

With stirring, 107.7 parts (2.20 moles) of sodium cyanide and 3.64 parts (0.01 mole) of cetyltrimethylammonium bromide are dissolved at 60° C. in 200 ml of deionised water. To the turbid solution are then added 175.1 parts (1 mole) of fused o-xylylene dichloride of 60° C. The temperature of the reaction mixture is kept between 60° and 65° C. with cooling, whereupon sodium chloride precipitates. The yellowish suspension is further stirred for 2 hours at 60°–65° C., cooled to 50° C. and diluted with 150 ml of deionised water. The reaction mixture is slowly cooled, with stirring, to 20° C. The precipitated crystalline product is collected by suction filtration, washed in portions with 1000ml of deionised water and dried in vacuo at 30° to 40° C., affording 156.8 parts of a product which contains 152 parts (97.4% of theory) of o-phenylenediacetonitrile with a melting point of 56°–60° C.

EXAMPLE 2

With stirring, 107.7 parts (2.20 moles) of sodium cyanide and 3.5 parts (0.005 mole) of an emulsifier consisting of tetradecyltrimethylammonium chloride and dodecyltrimethylammonium chloride, as 40% solution in water/isopropanol, are dissolved at 60° C. in 200 ml of deionised water. To this solution are added 175.1 parts (1 mole) of fused o-xylylene dichloride of 60° C. The temperature of the reaction mixture is kept between 60° and 65° C. by cooling, whereupon sodium chloride precipitates. The yellowish suspension is further stirred for 2 hours at 60°–65° C., cooled to 50° C. and diluted with 150 ml of deionised water. The reaction mixture is slowly cooled, with stirring, to 20° C. The precipitated crystalline product is collected by suction filtration, washed in portions with 1000 ml of deionised water and dried in vacuo at 30°–40° C., affording 159 parts of a product which contains 154.9 parts (99.1% of theory) of o-phenylenediacetonitrile with a melting point of 56°–60° C.

EXAMPLE 3

113.6 g of 95% sodium cyanide and 7.1 g of benzyl tri-n-butyl-ammonium bromide are dissolved in 250 ml of water. The reaction mixture is heated to 95° C. and then treated under nitrogen in the course of 15 minutes, with good stirring, with 264 g of o-xylylene dibromide. The reaction is exothermic, the temperature of the reaction mixture remaining between 95° and 100° C. during the addition of the o-xylylene dibromide without the application of heat. After stirring for a further 30 minutes at 95° C. under nitrogen, the slightly brownish coloured reaction mixture is rapidly cooled to room temperature. The oily organic layer is taken up in methylene chloride, washed neutral with water and dried over sodium sulphate. The methylene chloride is removed in vacuo, affording 153 g of a light brown oil which analysis by gas chromatography shows to have a content of 85% (83% of theory) of o-phenylenediacetonitrile. On seeding with a few crystals of o-phenylenediacetonitrile, this oil crystallises at room temperature rapidly and with a slight exothermic reaction. Melting point: 55°–60° C.

EXAMPLE 4

The procedure of Example 3 is carried out using 4.5 g of dodecyltri-n-butylphosphonium bromide instead of 7.1 g of benzyltri-n-butylammonium bromide, affording 145 g of a light brown oil which analysis by gas chromatography shows to have a content of 88% (82% of theory) of o-phenylenediacetonitrile. On seeding with a few crystals of o-phenylenediacetonitrile, this oil crystallises at room temperature rapidly and with a slightly exothermic reaction. Melting point: 57°–60° C.

EXAMPLE 5

With stirring, 107.7 parts (2.20 moles) of sodium cyanide are dissolved at 60° C. in 200 ml of deionised water. To the resultant turbid solution are then added 175.1 parts (1 mole) of warm fused o-xylylene dichloride of 60° C. in the course of 4 hours, while keeping the temperature between 60° and 65° C. Towards the end of the addition, the temperature rises to approx. 110° C. and then falls again to 60°–65° C. The resultant mixture is further stirred for 17 hours at 60° to 65° C., diluted with 170 ml of deionised water and cooled to room temperature, whereupon the product crystallises out. After further cooling to 0° C. and keeping this temperature for 1 hour, the product is collected by suction filtration, washed in portions with 200 ml of ice-cold water and dried in vacuo at 30° to 40° C., affording 155 g of a product which contains 142 parts (90.8% of theory) of o-phenylenediacetonitrile with a melting point of 50°–54° C.

EXAMPLE 6

175.1 parts (1 mole) of o-xylylene dichloride are suspended in 170 ml of water and the suspension is emulsified, with vigorous stirring, at 60° to 65° C. in the presence of 3.5 parts (0.005 mole) of an emulsifier consisting of tetradecyltrimethylammonium chloride as a 40% solution in water/isopropanol. To this emulsion is then added a solution of 107.7 parts (2.20 moles) of sodium cyanide in 200 ml of deionised water. The temperature of the reaction mixture is kept between 60° and 65° C. by cooling. The yellowish brown suspension is further stirred for 2 hours at 60°–65° C., cooled to 30° C. and seeded with pure product. When crystallisation is complete, the mixture is cooled to 15° C., stirred for 1 hour at 15° C. and filtered with suction. The crystalline product is subsequently washed in portions with 500 ml of deionised water and dried in vacuo at 30° to 40° C., affording 159 parts of a product which contains 144.5 parts (92.5% of theory) of o-phenylenediacetonitrile with a melting point of 52°–54° C. Instead of the sodium cyanide solution it is also possible to use a corresponding potassium cyanide solution.

What we claim is:

1. A process for the manufacture of o-phenylenediacetonitrile by reaction of o-xylylene dichloride with alkali metal or alkaline earth metal cyanides, which comprises reacting an aqueous solution of alkali metal or alkaline earth metal cyanide with o-xylylene dichloride at temperatures between 50° and 70° C., in the presence of a cationic emulsifier, which is a quaternary phosphonium or ammonium compound selected from the group consisting of dodecyl tri-n-butylphosphonium bromide, cetyl- or lauryl- benzyldimethylammonium chloride, cetyltrimethylammonium bromide, benzyl tri-n-butylammonium bromide, hexadecyl(dichlorobenzyl)-dimethylammonium chloride, octadecyloxymethyl chloride, hexadecyloxymethylpyridinium chloride or lauryloxymethyl-N-β-hydroxyethylmorpholinium chloride.

2. A process according to claim 1 wherein 0.01 to 10% of emulsifier is used.

3. A process according to claim 1 wherein sodium or potassium cyanide is used as alkali metal cyanide.

4. A process according to claim 1 wherein the fused o-xylylene dichloride is added to the aqueous solution of alkali metal or alkaline earth metal cyanide which contains the emulsifier.

* * * * *